United States Patent [19]

Yukinaga et al.

[11] 4,028,376

[45] June 7, 1977

[54] 3-ALKYLISOXAZOLE DERIVATIVES AND HERBICIDES CONTAINING THEM

[75] Inventors: Hisajiro Yukinaga, Kusatsu; Shinzaburo Sumimoto; Ichiro Ishizuka, both of Osaka; Jitsuo Sugita, Ikeda, all of Japan

[73] Assignee: Shionogi & Co., Ltd., Osaka, Japan

[22] Filed: Sept. 23, 1975

[21] Appl. No.: 615,883

[30] Foreign Application Priority Data

Oct. 4, 1974 Japan ............................ 49-114839

[52] U.S. Cl. .................. 260/307 H; 260/247.1 M; 260/247.2 A; 260/293.67; 71/88; 71/94
[51] Int. Cl.² .......................................... C07D 1/14
[58] Field of Search ............... 260/307 H, 247.1 M, 260/247.2 A, 293.67

[56] References Cited

UNITED STATES PATENTS 3,547,940  12/1970  Brantley ................. 260/307 H
3,743,498  7/1973  Brantley .................. 260/307 H X

*Primary Examiner*—Donald G. Daus
*Assistant Examiner*—D. B. Springer
*Attorney, Agent, or Firm*—Wenderoth, Lind & Ponack

[57] ABSTRACT

3-alkylisoxazole derivatives represented by the formula:

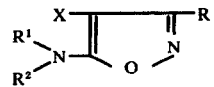

wherein R represents $C_3$–$C_6$ alkyl or $C_3$–$C_6$ cycloalkyl, $R^1$ represents hydrogen or $C_1$–$C_6$ alkyl, $R^2$ represents

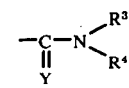

[in which $R^3$ and $R^4$ each represent hydrogen, $C_1$–$C_6$ alkyl, $C_2$–$C_7$ alkenyl, $C_1$–$C_6$ alkoxy, $C_2$–$C_7$ alkoxycarbonyl or $C_1$–$C_6$ alkylthio, or

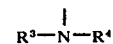

represents morpholino, pyrrolidino or piperidino, and Y represents oxygen or sulfur] or —CO—Y—$R^5$ [in which $R^5$ represents $C_1$–$C_6$ alkyl and Y is as defined above] and X represents hydrogen, halogen or $C_1$–$C_6$ alkyl, or R and X are combined to form $C_3$–$C_6$ alkylene, being useful as herbicides, are prepared by several routes.

11 Claims, No Drawings

3-ALKYLISOXAZOLE DERIVATIVES AND HERBICIDES CONTAINING THEM

The present invention relates to 3-alkylisoxazole derivatives and herbicides containing them. More particularly, this invention relates to 3-alkylisoxazole derivatives represented by the formula:

$$\underset{R^2}{\overset{R^1}{>}}N\underset{O}{\overset{X}{\bigvee}}\overset{R}{\underset{N}{\bigvee}} \quad (I)$$

wherein R represents $C_3$–$C_6$ alkyl or $C_3$–$C_6$ cycloalkyl, $R^1$ represents hydrogen or $C_1$–$C_6$ alkyl, $R^2$ represents $$-\underset{\underset{Y}{\|}}{C}-N\underset{R^4}{\overset{R^3}{<}}$$

[in which $R^3$ and $R^4$ each represent hydrogen, $C_1$–$C_6$ alkyl, $C_2$–$C_7$ alkenyl, $C_1$–$C_6$ alkoxy, $C_2$–$C_7$ alkoxycarbonyl or $C_1$–$C_6$ alkylthio, or $$R^3-\underset{|}{N}-R^4$$

represents morpholino, pyrrolidino or piperidino, and Y represents oxygen or sulfur] or —CO—Y—$R^5$ [in which $R^5$ represents $C_1$–$C_6$ alkyl and Y is as defined above] and X represents hydrogen, halogen or $C_1$–$C_6$ alkyl, or R and X are combined to form $C_3$–$C_6$ alkylene, and herbicides containing them as an effective ingredient.

The above terms are illustratively explained as follows: the alkyl involves methyl, ethyl, propyl, i-propyl, t-butyl, and pentyl (except methyl and ethyl if defined as $C_3$–$C_6$); the alkenyl involves vinyl, allyl, butenyl and butadienyl; the alkoxy involves methoxy, ethoxy, propoxy, butoxy and pentyloxy; the alkoxycarbonyl involves methoxycarbonyl, ethoxycarbonyl, propoxycarbonyl and butoxycarbonyl; the alkylthio involves methylthio, ethylthio, propylthio, butylthio, pentylthio, and hexylthio; the alkylene involves trimethylene, tetramethylene, and pentamethylene; and the halogen involves chlorine, bromine, fluorine and iodine.

As herbicides, 3-methyl-5-isoxazolylureas and 3-ethyl-5-isoxazolylureas have heretofore been known [U.S. Pat. Nos. 3,547,940; 3,743,498].

As the result of various investigations on the herbicidal activity of various isoxazole derivatives, the present inventors have discovered that the isoxazole derivatives (I) with $C_3$–$C_6$ alkyl or $C_3$–$C_6$ cycloalkyl at the 3-position show in the far more potent in the herbicidal activity than the said known herbicidal substances, with very low toxicity to humans, domestic animals, fowls, fishes and shells, and that they can be smoothly decomposed or degraded in soil to a suitable extent. Thus, the present invention has been established.

The 3-alkylisoxazole derivatives (I) of the present invention involve two types of compounds (urea type and carbamate type). The urea type compound is represented by the formula:

$$\underset{R^4}{\overset{R^3}{>}}N-\underset{\underset{Y}{\|}}{C}-\underset{|}{\overset{}{N}}\underset{R^1}{\overset{X}{\bigvee}}\overset{R}{\underset{N}{\bigvee}} \quad (Ia)$$

wherein R, $R^1$, $R^3$, $R^4$, X and Y are each as defined above, and the carbamate type compound is represented by the formula:

$$R^5-Y-CO-\underset{R^1}{\overset{}{N}}\underset{O}{\overset{X}{\bigvee}}\overset{R}{\underset{N}{\bigvee}} \quad (Ib)$$

wherein R, $R^1$, $R^5$, X and Y are each as defined above. These isoxazole derivatives (I), (Ia) and (Ib) can be prepared according to the following reaction scheme:

First Route

$$\underset{R^2}{\overset{R^1}{>}}N\underset{O}{\overset{}{\bigvee}}\overset{R}{\underset{N}{\bigvee}} \quad \xrightarrow{\text{Halogenation}}$$

(I) (X = Hydrogen)

$$\underset{R^2}{\overset{R^1}{>}}N\underset{O}{\overset{X}{\bigvee}}\overset{R}{\underset{N}{\bigvee}}$$

(I) (X = Halogen)

This route is the halogenation at the 4-position of the isoxazole ring which includes chlorination, bromination and iodination. These reactions are carried out in a conventional manner, adopting conventional halogenating agents, catalysts, solvents and temperature conditions.

Second Route

$$\underset{R^2}{\overset{R^1}{>}}N\underset{O}{\overset{X}{\bigvee}}\overset{R}{\underset{N}{\bigvee}} \quad \xrightarrow{\text{N-Alkylation}}$$

(I)
[At least one hydrogen exists on the nitrogen of the side chain.]

$$\underset{R^2}{\overset{R^1}{>}}N\underset{O}{\overset{X}{\bigvee}}\overset{R}{\underset{N}{\bigvee}}$$

(I)
[At least one alkyl group is introduced on the nitrogen.]

This route is the alkylation of the active nitrogen in the side chain. Ordinary N-alkylating agents can be used in general. Explaining the methylation illustratively, methyl halide (e.g. methyl bromide, methyl iodide), dimethylsulfate, diazomethane, organic sulfonic acid ester (e.g. methyl methanesulfonate, methyl toluenesulfonate), a mixture of formaldehyde and formic acid, and a combination of formaldehyde and reducing agent may be used. This N-alkylation may be effected in a conventional manner.

Third Route:

$$OCN\underset{O}{\overset{X}{\bigvee}}\overset{R}{\underset{N}{\bigvee}} \quad \xrightarrow{R^3NHR^4 (III)}$$

(II)

-continued

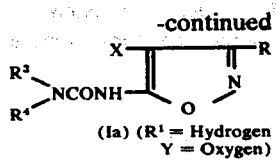

(Ia) (R¹ = Hydrogen
Y = Oxygen)

This route may be effected by reacting the 5-isoxazolyl isocyanate (II) with the amine (III) in an inert solvent (e.g. benzene, toluene, dioxane, diglyme, dimethylformamide) at room temperature or under cooling or heating, if necessary, in the presence of a basic catalyst (e.g. pyridine, triethylamine).

Fourth Route:

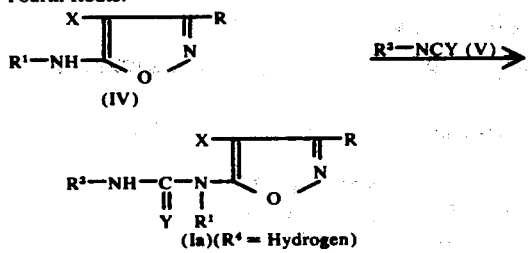

This route may be effected by reacting the amine (IV) with the isocyanate or isothiocyanate (V). The reaction is carried out as in Third Route.

Fifth Route:

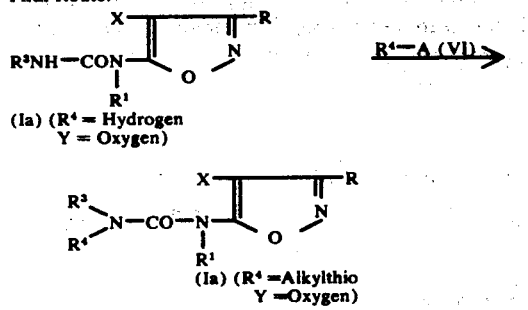

wherein A represents a reactive group (e.g. halogen or an ester residue). This route is effected by treating the urea (Ia) having an active nitrogen with the reagent (VI) such as alkylsulfenyl halide in a suitable solvent (e.g. pyridine, benzene) at room temperature or under cooling.

Sixth Route:

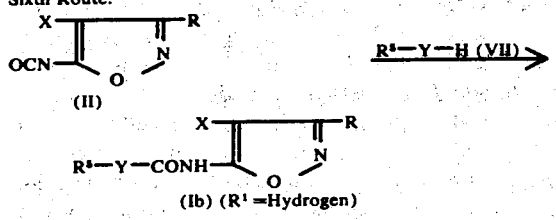

The route is effected by reacting the 5-isoxazolyl isocyanate (II) with the alcohol or mercaptan (VII). The reaction is carried out as in Third Route.

Seventh Route:

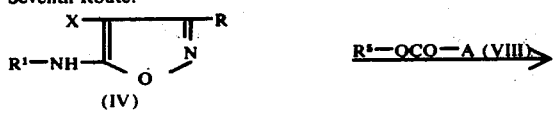

-continued

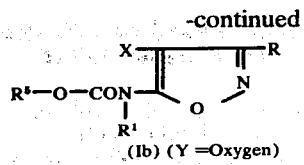

(Ib) (Y = Oxygen)

This route is effected by reacting the 5-isoxazolylamine (IV) with the reactive derivative (e.g. halogenide, ester) of carbonic acid (VIII) in the presence of a base (e.g. pyridine, triethylamine) in the presence or absence or an inert solvent (e.g. dimethylformamide, chloroform, tetrahydrofuran, benzene) at room temperature or under heating.

Practical embodiments of the preparation of the isoxazole derivatives (I) in each route are illustratively shown in the following synthetic examples.

SYNTHETIC EXAMPLE 1

Into a solution of 3-t-butyl-5-isoxazolyl isocyanate (2.84 g) in toluene (51 ml) is introduced methylamine (1.58 g) at room temperature. The mixture is stirred at room temperature for 2 hours and then at 50° C for 4 hours. The reaction mixture is evaporated to remove the solvent, and the residue is recrystallized from ethyl acetate to give 1-methyl-3-(3-t-butyl-5-isoxazolyl)urea (2.80 g) as crystals melting at 195.0° to 196.0° C (decomp.). The yield is 83.6%.

SYNTHETIC EXAMPLES 2 to 15

Using the following starting materials (II), the reactions are repeated as in Synthetic Example 1, whereby the corresponding products (Ia) are obtained.

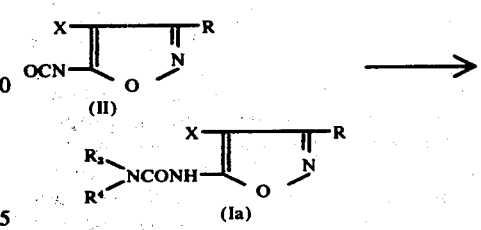

Table 1.

| Synthetic Ex. No. | II R | Ia R³ | R⁴ | M.P., B.P. or IR |
|---|---|---|---|---|
| 2 | Pr | Me | Me | 72.5–73.5 |
| 3 | Pr | Me | Met | 1727, 1617 cm⁻¹(CCl₄) |
| 4 | i-Pr | H | Me | 163.0–164.0 |
| 5 | i-Pr | Me | Al | 51.5–52.5 |
| 6 | i-Pr | Me | Met | 80.0–81.0 |
| 7 | i-Bu | Me | Me | 128.5–129.0 |
| 8 | i-Bu | Me | Bu | 1701, 1618 cm⁻¹(CCl₄) |
| 9 | t-Bu | H | H | 176.0–177.0(d) |
| 10 | t-Bu | Me | Me | 125.5–126.0 |
| 11 | t-Bu | Me | Bu | 86.0–87.0 |
| 12 | t-Bu | Me | Met | 105.5–106.0 |
| 13 | t-Bu | (—CH₂CH₂)₂O | | 165.0–166.0 |
| 14 | C-Pr | Me | Me | 129.0–130.0 |
| 15 | —(CH₂)₄— | Me | Me | 124.5–125.5 |

Note: The abbreviations in the table have the following significance: H (Hydrogen), Me (Methyl group), Et (Ethyl group), Pr (Propyl group), Bu (Butyl group), Met (Methoxy group), Al (Allyl group), C- (Cyclo-), i- (Iso-), t- (Tertiary-), M.P. (Melting point, ° C), B.P. (Boiling point), IR (Infrared absorption spectra).

SYNTHETIC EXAMPLE 16

A mixture of 3-t-butyl-5-methylaminoisoxazole (2.16 g) and methyl isocyanate (1.04 g) is heated at 80° C in a sealed tube for 13 hours. Then, methyl isocyanate (0.40 g) is added thereto, and the resultant mixture is heated at 80° C for 9 hours. The reaction mixture is chromatographed on a column of silica gel, whereby 1,3-dimethyl-3-(3-t-butyl-5-isoxazolyl)-urea (2.56 g) is obtained. The yield is 86.3%. IR: 1700, 1598 cm$^{-1}$ (CCl$_4$).

SYNTHETIC EXAMPLE 17

To a solution of 3-t-butyl-5-isoxazolyl isocyanate (11.63 g) in toluene (154 ml), methanol (20 ml) and triethylamine (3 drops) are added, and the resultant mixture is stirred at 80° C for 3 hours. The reaction mixture is evaporated to remove the low boiling materials, and the residue is recrystallized from n-hexane to give methyl 3-t-butyl-5-isoxazolylcarbamate (12.17 g) as crystals melting at 86.5° to 87° C.

SYNTHETIC EXAMPLE 18

Using 3-t-butyl-5-isoxazolyl isocyanate and methyl mercaptan, the reaction is effected as in Synthetic Example 17, whereby S-methyl 3-t-butyl-5-isoxazolylthiocarbamate is obtained as crystals melting at 104.0° to 105.5° C.

SYNTHETIC EXAMPLE 19

To a solution of metallic sodium (0.42 g) in methanol (12 ml), a solution of methyl 3-t-butyl-5-isoxazolylcarbamate (3.47 g) in methanol (5.5 ml) is added, and the resultant mixture is stirred at room temperature for 10 minutes. The reaction mixture is evaporated under reduced pressure to remove the methanol. The residue is combined with benzene, which is then evaporated. The residue is again combined with benzene (27 ml), and dimethyl sulfate (2.32 g) is added dropwise. The resultant mixture is stirred at room temperature for 1 hour and then refluxed for 1 hour. After cooling, the reaction mixture is filtered to remove the precipitate. The filtrate is washed with aqueous sodium bicarbonate solution and then water, dried over anhydrous sodium sulfate and evaporated to remove the solvent. The residue is recrystallized from cyclohexanone to give methyl N-methyl-3-t-butyl-5-isoxazolylcarbamate (3.41 g) as crystals melting at 70.5° to 71.5° C. The yield is 91.8%.

SYNTHETIC EXAMPLE 20

To a solution of 1,1-dimethyl-3-(3-propyl-5-isoxazolyl)urea (2.76 g) in dimethylformamide (26 ml) dried over molecular sieve, 50% sodium hydride (0.74 g) is added, and the resultant mixture is stirred at 60° C for 15 minutes. The mixture is cooled at 10° C, and a solution of methyl iodide (2.38 g) in dry dimethylformamide (5 ml) is added dropwise in an hour thereto. The resultant mixture is heated at 80° C for 5 minutes. The reaction mixture is evaporated to remove the solvent. The residue is mixed with water (30 ml) and shaken with chloroform. The organic layer is washed with water, dried over anhydrous sodium sulfate and evaporated to remove the solvent. The residue is chromatographed on a column of silica gel, whereby 1,1,3-trimethyl-3-(3-propyl-5-isoxazolyl)urea (2.75 g) is obtained as an oil boiling at 116.0° to 117.0° C/0.63 mm Hg. The yield is 93.0%.

SYNTHETIC EXAMPLE 21

Using 1,1-dimethyl-3-(3-t-butyl-5-isoxazolyl)urea, the reaction is effected as in Synthetic Example 20, whereby 1,1,3-trimethyl-3-(3-t-butyl-5-isoxazolyl)urea is obtained as crystals melting at 72.0° to 73.0° C.

SYNTHETIC EXAMPLE 22

To a mixture of 1,1-dimethyl-(3-t-butyl-5-isoxazolyl)-urea (0.70 g), anhydrous sodium acetate (0.30 g) and glacial acetic acid (3.3 ml), bromine (0.53 g) is added dropwise in 10 minutes with ice cooling and stirring and the resultant mixture is stirred for 15 minutes. The reaction mixture is poured into ice water (30 ml) and shaken with methylene chloride. The organic layer is washed with saturated aqueous sodium bicarbonate solution and then water and evaporated to remove the solvent. The residue is recrystallized from benzene to give 1,1-dimethyl-3-(3-t-butyl-4-bromo-5-isoxazolyl)urea (0.96 g) as crystals melting at 175.5° to 176.5° C (decomp.).

SYNTHETIC EXAMPLE 23

To a solution of methyl 3-t-butyl-5-isoxazolylcarbamate (2.56 g) in methylene chloride (13 ml), sulfuryl chloride (1.81 g) is added dropwise, and the resultant mixture is refluxed for 2 hours. The reaction mixture is evaporated to remove the solvent, whereby methyl 3-t-butyl-4-chloro-5-isoxazolylcarbamate (3.08 g) is obtained as an oil. IR: 1748, 1642 cm$^{-1}$ (CCl$_4$).

SYNTHETIC EXAMPLE 24

Using 1-methyl-3-(3-t-butyl-5-isoxazolyl)urea, the reaction is effected as in Synthetic Example 23, whereby 1-methyl-3-(3-t-butyl-4-chloro-5-isoxazolyl)urea is obtained as crystals melting at 169.0° to 170.5° C (decomp.).

SYNTHETIC EXAMPLE 25

To a solution of 1-methyl-3-(3-t-butyl-5-isoxazolyl)-urea (0.99 g) in pyridine (8 ml), butylsulfenyl chloride (0.67 g) is added dropwise at −30° to −40° C, and the resultant mixture is stirred at the same temperature for 6 hours. The reaction mixture is allowed to stand at room temperature overnight, poured into ice water and shaken with benzene. The organic layer is washed with 3% hydrochloric acid, 5% aqueous sodium bicarbonate solution and water in that order, dried over anhydrous sodium sulfate and evaporated to remove the solvent. The residue is chromatographed on a column of silica gel, whereby 1-methyl-1-butylthio-3-(3-t-butyl-5-isoxazolyl)urea (0.031 g) is obtained as an oil. IR: 1712, 1617 cm$^{-1}$ (CCl$_4$).

SYNTHETIC EXAMPLE 26

A mixture of 3-t-butyl-5-aminoisoxazole (2.07 g), methyl isothiocyanate (1.40 g) and triethylamine (3 drops) is heated at 75° C for 72 hours. The reaction mixture is chromatographed on a column of silica gel, whereby 1-methyl-3-(3-t-butyl-5-isoxazolyl)thiourea (1.66 g) is obtained as an oil. IR: 1622 cm$^{-1}$ (CCl$_4$).

These isoxazole derivatives (I) show an excellent herbicidal activity against various grasses in a small application rate, and they can be used as a non-selective or selective herbicide by changing the application rate of the effective compound. The herbicides of this invention are generally applicable over various crops including wheat, barley, corn, carrot, peanut, peas or rice plant. They can be applied over sugar cane, potato, sweet potato, mentha, egg-plant, or Spanish paprika after planting these crops. There is almost no chemical harm caused by the present herbicides on these crops, but if any is observed, it is only very slight, to an extent which permits the crops to recover easily. Still, they are harmless and safe to humans, domestic animals and fowls and show a very low toxicity to fishes and shells. Accordingly, the herbicides of the present invention are very safe and show a permissible degree of residue in soil.

The present herbicides may be prepared by mixing the effective isoxazole derivatives (I) with a suitable inert solid or liquid carrier, optionally in combination with a further adjuvant (e.g. emulsifiers, stabilizers, dispersants, suspending agents, spreaders, penetrants, wetting agents) and converting the resultant mixture into a desired form of preparation (e.g. emulsions, wettable powders, granules, dusts, pills). Examples of the carrier are a solid carrier (e.g. clay, talc, diatomaceous earth, bentonite) and a liquid carrier (e.g. water, alcohols, acetone, benzene, toluene, xylene, solvent naphtha, cyclohexane).

The herbicides of the present invention may be also used in combination with agricultural chemicals (e.g. insecticides, fungicides, other herbicides), manuring ingredients (e.g. ammonium sulfate, urea), or soil treating agents.

Herbicidal activities of the present herbicides are shown illustratively by the following experimental examples.

Experimental Example a) Compounds tested:

| Compound No. | Compound Name |
|---|---|
| 1 | 1-methyl-1-butyl-3-(3-t-butyl-5-isoxazolyl)urea |
| 2 | 1-methyl-3-(3-t-butyl-5-isoxazolyl)urea |
| 3 | 1,1-dimethyl-3-(3-t-butyl-5-isoxazolyl)urea |
| 4 | 1,1,3-trimethyl-3-(3-t-butyl-5-isoxazolyl)-urea |
| 5 | 1,3-dimethyl-3-(3-t-butyl-5-isoxazolyl)urea |
| 6 | 1-methyl-1-methoxy-3-(3-t-butyl-5-isoxazolyl)-urea |
| 7 | 1-methyl-1-methoxy-3-(3-i-propyl-5-isoxazolyl)-urea |
| 8 | methyl N-(3-t-butyl-4-chloro-5-isoxazolyl)-carbamate |
| 9 | 1-methyl-3-(3-t-butyl-4-chloro-5-isoxazolyl)-urea |
| 10 | 1,1-dimethyl-3-(3-t-butyl-4-bromo-5-isoxazolyl)-urea |
| 11 | PCP-Na (sodium pentachlorophenoxide)(Commercially available herbicide) |
| 12 | 1-phenyl-3-(3-methyl-4-bromo-5-isoxazolyl)urea (Compound described in U.S. Pat. No. 3,547,940) | b. Test method:

1. Pre-emergence test:

In a polyethylene cup (diameter: 9 cm) in which sandy soil was charged, 25 granules of the seed of the test plant were sown for each species. After sowing, the seed was covered with sandy soil, about 5 mm in thickness, and soon an aqueous suspension of the test compound made by using as a spreader Tween 20 at a concentration of 100 ppm was applied over the surface of the sandy soil. Application rate of the test compound was 10 g/are and 30 g/are, and the aqueous suspension (water dilution: 10 L/are) was applied by a sprayer. Administration was effected at 25° C in a greenhouse in the natural sunlight. Degree of the germination was measured 3 weeks after the application.

2. Post-emergence test:

As in the pre-emergence test, the test compound was applied to young plants 10 days after seeding. Administration and measurement were effected as described above.

c. Method of the evaluation:

The resultant was obtained by observing the plant with the naked eye after the application and calculating the survival ratio of the number of living plants three weeks later. The evaluation was marked in six degrees on the survival ratio, as follows:

| Survival ratio of the plant tested | Mark (s) |
|---|---|
| Not more than 10 % | 5 |
| 11–25 % | 4 |
| 26–50 % | 3 |
| 51–75 % | 2 |
| 76–90 % | 1 |
| 91–100 % | 0 | d) Result:

Table 2.

| Compound No. | Application rate (g/are) | Pre-emergence test | | | | | | Post-emergence test | | | | | |
|---|---|---|---|---|---|---|---|---|---|---|---|---|---|
| | | A | B | C | D | E | F | A | B | C | D | E | F |
| 1 | 10 | 0 | 3 | 3 | 5 | 5 | 5 | 0 | 3 | 3 | 5 | 5 | 5 |
| | 30 | 0 | 5 | 3 | 5 | 5 | 5 | 0 | 5 | 5 | 5 | 5 | 5 |
| 2 | 10 | 0 | 0 | 2 | 4 | 3 | 5 | 0 | 2 | 3 | 5 | 5 | 5 |
| | 30 | 0 | 2 | 4 | 5 | 5 | 5 | 0 | 3 | 5 | 5 | 5 | 5 |
| 3 | 10 | 0 | 1 | 4 | 5 | 5 | 5 | 1 | 3 | 4 | 5 | 5 | 5 |
| | 30 | 1 | 3 | 5 | 5 | 5 | 5 | 1 | 5 | 5 | 5 | 5 | 5 |
| 4 | 10 | 0 | 1 | 2 | 5 | 5 | 3 | 0 | 0 | 0 | 5 | 5 | 5 |
| | 30 | 0 | 1 | 3 | 5 | 5 | 4 | 0 | 1 | 2 | 5 | 5 | 5 |
| 5 | 10 | 0 | 2 | 5 | 5 | 5 | 5 | 0 | 3 | 3 | 5 | 5 | 5 |
| | 30 | 0 | 3 | 4 | 5 | 5 | 5 | 0 | 5 | 5 | 5 | 5 | 5 |
| 6 | 10 | 0 | 3 | 5 | 5 | 5 | 5 | 0 | 2 | 2 | 5 | 5 | 5 |
| | 30 | 0 | 5 | 5 | 5 | 5 | 5 | 0 | 5 | 5 | 5 | 5 | 5 |
| 7 | 10 | 0 | 0 | 3 | 2 | 5 | 5 | 0 | 0 | 1 | 5 | 4 | 5 |
| | 30 | 0 | 3 | 5 | 5 | 5 | 5 | 0 | 2 | 3 | 5 | 5 | 5 |
| 8 | 10 | 0 | 0 | 0 | 4 | 4 | 4 | 0 | 0 | 0 | 2 | 2 | 5 |
| | 30 | 0 | 1 | 2 | 5 | 5 | 5 | 0 | 1 | 1 | 5 | 5 | 5 |
| 9 | 10 | 0 | 2 | 4 | 5 | 5 | 5 | 0 | 0 | 2 | 5 | 1 | 4 |
| | 30 | 0 | 2 | 5 | 5 | 5 | 5 | 0 | 1 | 2 | 5 | 3 | 5 |
| 10 | 10 | 0 | 0 | 0 | 4 | 0 | 4 | 0 | 1 | 1 | 5 | 4 | 5 |
| | 30 | 0 | 1 | 1 | 5 | 5 | 5 | 0 | 1 | 1 | 5 | 5 | 5 |
| 11 | 10 | 0 | 0 | 0 | 0 | 2 | 3 | 0 | 0 | 0 | 0 | 2 | 5 |
| | 30 | 0 | 0 | 0 | 0 | 2 | 3 | 0 | 0 | 0 | 0 | 4 | 5 |
| 12 | 10 | 0 | 0 | 0 | 0 | 1 | 1 | 0 | 0 | 0 | 0 | 0 | 1 |
| | 30 | 0 | 0 | 0 | 0 | 0 | 2 | 0 | 0 | 0 | 0 | 0 | 0 |

Note: The abbreviations have the following significance:
A (Triticum aestivum), B (echinochloa crusgalli),
C (Digitaria adscendens), D (Brassica campestris),
E (Polygonum logisetum), F (Amaranthus retroflexus).

Accordingly, each of the compounds of this invention (Compound Nos. 1–10) hardly show herbicidal activity to Triticum aestivum but generally show an excellent and selective herbicidal activity to Echinochloa crusgalli, Digitaria adscendens, Brassica campestris, Polygonum longisetum and Amaranthus retroflexus, being by far more potent than PCP-Na (Compound No. 11), a commercially available herbicide, and 1-phenyl-3-(3-methyl-4-bromo-5-isoxazolyl)urea (Compound No. 12) described in U.S. Pat. No. 3,547,940.

Practical embodiments of the present herbicides are illustratively shown in the following examples.

EXAMPLE 1

1-methyl-1-butyl-3-(3-t-butyl-5-isoxazolyl)urea (10 parts by weight), Sorpol (Registered trademark; made by Toho Chemical Industry, Co., Ltd.) (10 parts by weight), cyclohexanone (20 parts by weight) and solvent naphtha (60 parts by weight) are admixed and dissolved, whereby an emulsion is obtained.

EXAMPLE 2

1,1,3-trimethyl-3-(3-t-butyl-5-isoxazolyl)urea (50 parts by weight), calcium ligninsulfonate (3 parts by weight), Sorpol (3 parts by weight) and diatomaceous earth (44 parts by weight) are admixed and pulverized, whereby a wettable powder is obtained.

EXAMPLE 3

1-methyl-1-methoxy-3-(3-t-butyl-5-isoxazolyl)urea (5 parts by weight) and clay (95 parts by weight) are admixed and pulverized, whereby a dust is obtained.

EXAMPLE 4

1-methyl-1-methoxy-3-(3-i-propyl-5-isoxazolyl)urea (5 parts by weight), calcium ligninsulfonate (5 parts by weight), bentonite (30 parts by weight) and clay (60 parts by weight) are admixed and pulverized, mixed with water, kneaded, granulated and dried, whereby granules are obtained.

What is claimed is:

1. A compound of the formula

wherein R represents alkyl of 3–6 carbon atoms or cycloalkyl of 3–6 carbon atoms,
$R^1$ represents hydrogen or alkyl of 1–6 carbon atoms,
$R^3$ represents hydrogen or alkyl of 1–6 carbon atoms,
$R^4$ represents hydrogen, alkyl of 1–6 carbon atoms, alkenyl of 2–7 carbon atoms, alkoxy of 1–6 carbon atoms or alkylthio of 1–6 carbon atoms, or
$R^3$ and $R^4$ are combined to form, together with the nitrogen atom to which they are attached, morpholino, pyrrolidino or piperidino,
X represents hydrogen or halogen, and
Y represents oxygen or sulfur, or
R and X are combined to form alkylene of 3–6 carbon atoms.

2. A compound according to claim 1, namely 1-methyl-1-butyl-3-(3-t-butyl-5-isoxazolyl)urea.

3. A compound according to claim 1, namely 1-methyl-3-(3-t-butyl-5-isoxazolyl)urea.

4. A compound according to claim 1, namely 1,1-dimethyl-3-(3-t-butyl-5-isoxazolyl)urea.

5. A compound according to claim 1, namely 1,1,3-trimethyl-3-(3-t-butyl-5-isoxazolyl)urea.

6. A compound according to claim 1, namely 1,3-dimethyl-3-(3-t-butyl-5-isoxazolyl)urea.

7. A compound according to claim 1, namely 1-methyl-1-methoxy-3-(3-t-butyl-5-isoxazolyl)urea.

8. A compound according to claim 1, namely 1-methyl-1-methoxy-3-(3-i-propyl-5-isoxazolyl)urea.

9. A compound according to claim 1, namely 1-methyl-3-(3-t-butyl-4-chloro-5-isoxazolyl)urea.

10. A compound according to claim 1, namely 1,1-dimethyl-3-(3-t-butyl-4-bromo-5-isoxazolyl)urea.

11. A compound according to claim 1, wherein R represents alkyl of 3 or 4 carbon atoms or cycloalkyl of 3 or 4 carbon atoms,
$R^1$ represents hydrogen or alkyl of 1–3 carbon atoms,
$R^3$ represents hydrogen or alkyl of 1–3 carbon atoms,
$R^4$ represents hydrogen, alkyl of 1–3 carbon atoms, alkenyl of 2–5 carbon atoms, alkoxy of 1–3 carbon atoms or alkylthio of 1–3 carbon atoms,
X represents hydrogen or halogen, and
Y represents oxygen or sulfur, or
R and X are combined to form alkylene of 4 or 5 carbon atoms.

* * * * *